(12) United States Patent
Ettlin (10) Patent No.: US 10,695,505 B2
(45) Date of Patent: Jun. 30, 2020

(54) DUAL-CHAMBER SYRINGE

(71) Applicant: Sulzer Mixpac AG, Haag (CH)

(72) Inventor: Josef Ettlin, Eichberg (CH)

(73) Assignee: SULZER MIXPAC AG, Haag (CH)

( * ) Notice: Subject to any disclaimer, the term of this patent is extended or adjusted under 35 U.S.C. 154(b) by 117 days.

(21) Appl. No.: 15/520,697

(22) PCT Filed: Oct. 9, 2015

(86) PCT No.: PCT/EP2015/073441
§ 371 (c)(1),
(2) Date: Apr. 20, 2017

(87) PCT Pub. No.: WO2016/062563
PCT Pub. Date: Apr. 28, 2016

(65) Prior Publication Data
US 2017/0312449 A1    Nov. 2, 2017

(30) Foreign Application Priority Data

Oct. 21, 2014    (EP) ..................................... 14189799

(51) Int. Cl.
*A61M 5/31*    (2006.01)
*A61M 5/315*    (2006.01)
(Continued)

(52) U.S. Cl.
CPC ...... *A61M 5/31596* (2013.01); *A61M 5/2448* (2013.01); *A61M 5/284* (2013.01);
(Continued)

(58) Field of Classification Search
CPC .. A61C 5/62; A61C 5/64; A61M 2005/31598; A61M 5/31596; A61M 5/284; A61M 5/2448; A61M 5/31511
See application file for complete search history.

(56) References Cited

U.S. PATENT DOCUMENTS 1,557,836 A * 10/1925 Hein ...................... A61M 5/24
                                                            604/237
2,567,001 A *  9/1951 Watson ................. A61M 5/283
                                                            604/192

(Continued)

FOREIGN PATENT DOCUMENTS

DE          1291859 B     4/1969
DE     102011107764 A1    1/2013

(Continued)

OTHER PUBLICATIONS

International Preliminary Report on Patentability dated Apr. 25, 2017 in corresponding International Application No. PCT/EP2015/073441, filed Oct. 9, 2015.

*Primary Examiner* — Scott J Medway
(74) *Attorney, Agent, or Firm* — Global IP Counselors, LLP (57) ABSTRACT

A discharger comprising a housing, a piston arranged inside the housing and being movable between a first piston position and a second piston position, a hollow cylindrical container inside the housing, the container being movable between a first container position and a second container position, a first compartment defined within the housing, a second compartment defined within the container, an axially extending passage in the interior of the piston and in communication with the first compartment and a peripheral opening of the piston in the region of a proximal end of the piston, a sealing element configured to prevent communication between the second compartment and the peripheral opening of the piston when the container is in a first container position, and a releasable retaining device configured to retain the piston in a piston first position until the container has reached a second container position.

19 Claims, 4 Drawing Sheets

(51) Int. Cl.
  *A61M 5/24* (2006.01)
  *A61M 5/28* (2006.01)
  *A61M 5/32* (2006.01)

(52) U.S. Cl.
  CPC ............... *A61M 5/32* (2013.01); *A61M 5/283* (2013.01); *A61M 2005/2451* (2013.01); *A61M 2005/31598* (2013.01)

(56) References Cited

U.S. PATENT DOCUMENTS

| | | | | |
|---|---|---|---|---|
| 2,684,068 A * | 7/1954 | Orens | ............... | A61M 5/284 604/88 |
| 2,841,145 A * | 7/1958 | Epps | ............... | A61M 5/284 604/89 |
| 2,842,126 A * | 7/1958 | Brown | ............... | A61M 5/288 604/201 |
| 2,954,767 A * | 10/1960 | Rane | ............... | A61M 5/31513 604/222 |
| 3,380,451 A | 4/1968 | Porter et al. | | |
| 3,477,432 A * | 11/1969 | Shaw | ............... | A61M 5/31596 604/91 |
| 3,489,147 A * | 1/1970 | Shaw | ............... | A61J 1/2093 222/137 |
| 3,542,023 A * | 11/1970 | Ogle | ............... | A61J 1/2096 604/88 |
| 3,570,486 A * | 3/1971 | Engelsher | ............... | A61M 5/2429 604/88 |
| 3,659,749 A * | 5/1972 | Schwartz | ............... | A61M 5/31596 222/129 |
| 3,678,931 A * | 7/1972 | Cohen | ............... | A61M 5/284 604/201 |
| 3,685,514 A * | 8/1972 | Cheney | ............... | A61M 5/31596 604/90 |
| 3,718,139 A * | 2/1973 | Hanford | ............... | A61M 5/31596 604/87 |
| 3,724,460 A | 4/1973 | Gomez et al. | | |
| 3,946,732 A * | 3/1976 | Hurscham | ............... | A61J 1/2093 604/88 |
| 3,977,568 A * | 8/1976 | Smith | ............... | B01L 3/0268 222/207 |
| 3,985,122 A * | 10/1976 | Topham | ............... | A61B 5/15003 600/578 |
| 4,060,082 A * | 11/1977 | Lindberg | ............... | A61M 5/284 141/388 |
| 4,331,146 A * | 5/1982 | Brignola | ............... | A61M 5/286 604/200 |
| 4,371,094 A | 2/1983 | Hutter, III | | |
| 4,581,016 A * | 4/1986 | Gettig | ............... | A61M 5/31596 604/88 |
| 4,599,082 A | 7/1986 | Grimard | | |
| 4,610,669 A | 9/1986 | Meyer et al. | | |
| 4,613,326 A | 9/1986 | Szware | | |
| 4,693,706 A | 9/1987 | Ennis, III | | |
| 4,861,335 A * | 8/1989 | Reynolds | ............... | A61M 5/2448 604/191 |
| 4,886,495 A * | 12/1989 | Reynolds | ............... | A61M 5/284 604/88 |
| 5,188,615 A * | 2/1993 | Haber | ............... | A61J 1/2093 604/203 |
| 5,372,586 A * | 12/1994 | Haber | ............... | A61M 5/31596 604/191 |
| 5,569,193 A | 10/1996 | Hofstetter et al. | | |
| 5,685,846 A | 11/1997 | Michaels, Jr. | | |
| 5,788,670 A | 8/1998 | Reinhard et al. | | |
| 6,602,223 B2 * | 8/2003 | Szapiro | ............... | A61M 5/284 604/89 |
| 6,997,357 B2 * | 2/2006 | Fuchs | ............... | A61M 15/0028 206/222 |
| 7,018,089 B2 | 3/2006 | Wenz et al. | | |
| 7,951,108 B2 * | 5/2011 | Harper | ............... | A61M 5/31596 604/191 |
| 8,100,597 B2 | 1/2012 | Sogaro | | |
| 8,556,848 B2 * | 10/2013 | Klug | ............... | A61M 5/31596 604/89 |
| 8,992,505 B2 * | 3/2015 | Thorne, Jr. | ............... | A61M 5/31596 604/122 |
| 9,586,008 B2 * | 3/2017 | Shetty | ............... | A61M 5/31596 |
| 9,872,962 B2 * | 1/2018 | Granelli | ............... | A61M 5/31596 |
| 9,878,106 B2 * | 1/2018 | Naftalovitz | ............... | A61M 5/31596 |
| 2002/0160333 A1 * | 10/2002 | Pierson | ............... | B05C 17/00516 433/90 |
| 2005/0177100 A1 | 8/2005 | Harper | | |
| 2006/0100587 A1 | 5/2006 | Bertron et al. | | |
| 2007/0083162 A1 * | 4/2007 | O'Reagan | ............... | A61M 39/26 604/167.03 |
| 2014/0171862 A1 | 6/2014 | Weidner | | |

FOREIGN PATENT DOCUMENTS

| | | |
|---|---|---|
| EP | 0112574 A1 | 7/1984 |
| EP | 0150681 A2 | 8/1985 |
| EP | 1205196 A1 | 5/2002 |
| EP | 1743618 A1 | 1/2007 |
| JP | S62139668 A | 6/1987 |
| JP | 2004097472 A | 4/2004 |
| JP | 4144027 B2 | 9/2008 |
| WO | 2006123205 A1 | 11/2006 |
| WO | 2012115022 A1 | 8/2012 |

\* cited by examiner

DUAL-CHAMBER SYRINGE

CROSS-REFERENCE TO RELATED APPLICATIONS

This application is a U.S. National Stage application of International Application No. PCT/EP2015/073441, filed Oct. 9, 2015, which claims priority to EP Application No. 14189799.1, filed Oct. 21, 2014 the contents of each of which are hereby incorporated herein by reference.

BACKGROUND

Field of Invention

The present disclosure relates to a discharger, in particular expendable syringe, for discharging a predetermined amount of a substance comprising at least two components.

Background Information

Generally, dischargers such as expendable syringes for use in the medical, dental or veterinary field are known which comprise one or more compartments in which a medical, dental or veterinary agent or a liquid including the medical, dental or veterinary agent is contained before use.

SUMMARY

The handling of existing dischargers is often complicated, especially if components are to be mixed or if a component is to be wetted by a fluid. Often, an additional apparatus is necessary for shaking the components.

Before this background, one object of the present disclosure is to provide a discharger, in particular expendable syringe, for discharging a predetermined amount of a substance comprising at least two components which has a compact structure as well as an ergonomic and aesthetic design, which can be easily handled, and which offers high reliability.

Accordingly, the present disclosure relates to a discharger, in particular expendable syringe, for discharging a predetermined amount of a substance comprising at least two components, the discharger comprising a housing defining a longitudinal axis and having a proximal and a distal end, a piston arranged at least partly inside said housing and being axially movable relative thereto between a first and a second position, a hollow cylindrical container arranged at least partly inside said housing, said container surrounding said piston and being axially moveable relative to said piston between a first and a second position, at least one first compartment defined within the housing between the distal end of the piston assuming its first position and the distal end of the housing for receiving at least one first component of the components, at least one second compartment defined within the container assuming its first position between the proximal end of the container and the proximal end of the piston for receiving at least one second component of the components, an axially extending passage disposed in the interior of the piston and being in communication with the first compartment and at least one peripheral opening of the piston in the region of the proximal end of the piston, a sealing element for preventing communication between the second compartment and the peripheral opening of the piston when the container assumes its first position, and a releasable retaining device for retaining the piston in its first position until the container has reached its second position, the discharger further being adapted so that communication between the second compartment and the peripheral opening of the piston is established after initiation of the movement of the container out of its first position towards its second position relative to the piston, thereby transferring the second component from the second compartment into the peripheral opening and through the passage of the piston into the first compartment the retaining device are released by the container reaching its second position, and with the further movement of the container into the housing and the simultaneous movement of the released piston out of its first position towards its second position, the at least two components are pressed out of the first compartment through the distal end of the housing.

The discharger may be adapted to be used in the medical, dental or veterinary field or in the health care sector. The present disclosure, however, is not limited in that way and can be used in other appliances in which it is desirable to discharge a predetermined amount of a substance comprising at least two components in an easy and reliable manner with the components being well-protected against environmental influences.

The discharger may be adapted to be used to discharge a substance obtained by a mixture of a powder and a fluid, or obtained by a granulate wetted by a fluid. The respective granulate can be used for establishing a bone structure in particular in the dental field. Even such an exemplary use for establishing a bone structure, however, is not limited to the dental field.

An advantage of the present disclosure is to avoid a special mixture apparatus or a special apparatus for shaking the compounds. The second component is transferred by pressure out of the second compartment into the first compartment where the components are, e.g., mixed or, e.g., one of the components is wetted by another component. For example, a respective powder may be dissolved in a fluid with the dissolution possibly being supported by shaking the discharger.

If the substance to be discharged contains a granulate, the outlet at the distal end of the housing of the discharger may be provided with a greater cross section. In this case, the cross section of the outlet may be equal to the cross section of the remainder of the housing of the discharger.

The discharger according to the present disclosure has a compact structure as well as an ergonomic and aesthetic design and can be easily handled only by pressing the container and subsequently also the piston further into the housing of the discharger in one direction.

Preferably, the container assuming its first position protrudes beyond the proximal end of the housing so as to be pushable further onto the piston out of its first position into its second position.

In an embodiment the piston assuming its first position protrudes beyond the proximal end of the housing so as to be pushable further into the housing out of its first position into its second position via the container assuming its second position relative to the piston. Thus, the piston finally can be pushed further into the housing via the container after the container has reached its second position relative to the piston and the second component has been pressed out of the second compartment into the first compartment.

The sealing element of the discharger may comprise a circumferentially extending projection which projects inwardly from the inner wall of the container towards the outer wall of the piston so as to sealingly close the peripheral opening of the piston when the container assumes its first position, and to contact the piston in a region located distal to the peripheral opening when the container assumes a position with the communication between the second compartment and the peripheral opening being established after initiation of the movement of the container out of its first position towards its second position relative to the piston. These simple and effective sealing element presents the second component from entering into the opening of the piston before the container starts to move towards its second position and, after initiation of the movement of the container, ensure that at least most of the second component gets into the opening of the piston instead of into the space between the container and the piston.

As soon as the communication between the second compartment and the peripheral opening of the piston is established, the second component can be transferred through the axially extending passage provided in the interior of the piston to the first compartment. Since the piston is held in its first position relative to the housing by the retaining device until the container has reached its second position relative to the piston, the necessary pressure for transferring the second component from the second compartment into the first compartment can be exercised by moving the container out of its first position into its second position relative to the piston.

The container may be adapted to be loaded with a cartridge defining the second compartment for storing the second component. In particular, but not exclusively, in such a case sealing means may be provided, comprising a seal, for example a foil, a membrane or the like, which is breakable with the movement of the container out of its first position towards its second position relative to the piston. In particular, such a breakable seal may be provided at the distal end of a respective cartridge storing the second component and being adapted to be loaded into the container. Alternatively, no cartridge is needed and the container is adapted to be filled directly with the second component, and the container may be open at its distal end and is only closed e.g. after having been filled by a user, for example immediately before using the discharger, with e.g. distilled water or another fluid by the proximal end of the piston.

Further alternatively, the container may be in the form of a cartridge which is loaded into or which is adapted to be loaded into the housing and which defines the second compartment for storing said second component.

The piston may have an axial length along the longitudinal axis which is approximately the same as the axial length of the housing and/or of the container, and/or which amounts to between 0.5 and 1.5 times, preferably to between 0.8 and 1.2 times, the axial length of the housing and/or of the container.

The piston may have an axial length along the longitudinal axis which is larger, in particular substantially larger, than its diameter as measured perpendicular to the longitudinal axis, and/or which amounts to more than 2 times, preferably to more than 4 times, even preferably to more than 6 times, its diameter as measured perpendicular to the longitudinal axis.

The axial length of the piston enables movements of the piston, the container and the housing relative to each other. In particular, a relevant axial length of the piston provides a relevant travel length of the container relative to the piston, which may be desired to transfer the second component from the container through the piston into the first compartment of the housing before the piston starts to press the two components out of the housing.

The releasable retaining device preferably comprises a, preferably peripherally extending, stop at the inner wall of the housing on which the rim of the distal end of the piston assuming its first position abuts until it is pushed out of engagement with the stop by the distal end of the container when the container reaches its second position.

Preferably, the distal end of the piston includes a conically shaped portion having an outer cross section increasing towards its distal end, the conically shaped portion of the piston being flexibly deformable by the distal end of the container reaching its second position so as to push the rim of the conically shaped portion of the piston out of engagement with the stop and to release the retaining device.

Consequently, the retaining device is released by the distal end of the container when the container reaches its second position. With the further movement of the container into the housing the released piston is simultaneously moved together with the container so as to press out the substance comprising the at least two components out of the first compartment through the distal end of the housing of the discharger.

The stop may be formed by a tapering of the inner cross section of the housing.

Preferably, the discharger is prefilled with or is adapted for being prefilled with at least one of the at least two components.

In one embodiment, the discharger is adapted so that the at least two components of the substance to be discharged may be mixed in the first compartment.

In another embodiment, the discharger is adapted so that one of the at least two components is wetted by another component of the at least two components in the first compartment.

The at least two components of the substance to be discharged may comprise at least one component in the form of a desiccant, e.g. a powder or a granulate, and/or at least one component in the form of a fluid, e.g. distilled water. The present disclosure is, however, not limited to such components. In a medical field of use, the first component within the first compartment may be or may comprise at least one vaccine and the second component within the second compartment may be or may comprise water or distilled water.

In another aspect, the present disclosure relates to a cartridge for a discharger according to any of the preceding claims, the cartridge including at least one second component which is adapted, together with a first component within the discharger, to form a substance to be discharged by the discharger.

In yet a further aspect, the present disclosure relates to a discharge system comprising a discharger as disclosed herein and at least one cartridge as disclosed herein, wherein the cartridge is loaded into or is adapted to be loaded into the container of the discharger, or wherein the cartridge is formed as the container of the discharger.

In another aspect, the present disclosure also relates to the use of a discharger as disclosed herein for discharging a substance including at least one medical, dental or veterinary agent. The present disclosure, however, is not limited to such a use.

Further embodiments of the present disclosure are also indicated in the description, in the claims as well as in the drawings.

The different embodiments of the discharger as described above as well as the individual features which are disclosed there and/or which are mentioned in the dependent claims may be combined with each other.

The discharger may be fabricated from any suitable material. In one embodiment, the material is plastic. The material may be selected from the group comprising PP, COC, PE, PA, PBT and PMMA. Alternatively, the material may be glass, metal or an alloy.

BRIEF DESCRIPTION OF THE DRAWINGS

Referring now to the attached drawings which form a part of this original disclosure.

DETAILED DESCRIPTION OF THE EMBODIMENTS

FIGS. 1 to 6 show an exemplary embodiment of a discharger 10, in particular expendable syringe, for discharging a predetermined amount of a substance comprising at least two components.

The discharger 10 comprises a cylindrical housing 12 defining a longitudinal axis 14 and having a proximal end 16 and a distal end 18, a piston 20, and a hollow cylindrical container 22. A removable cap 60 is associated with the distal end 18 of the housing 12.

Figure 1:
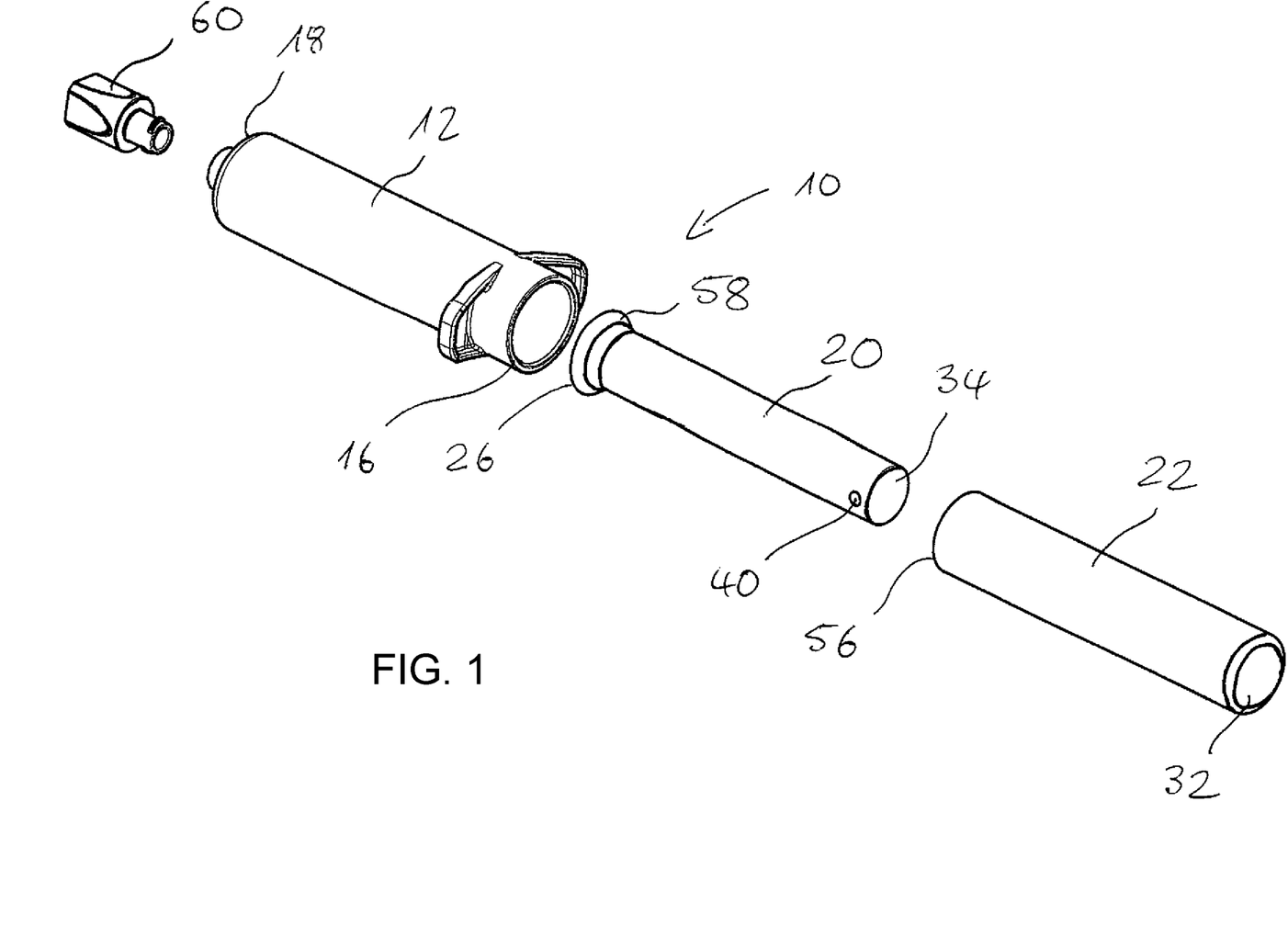
FIG. 1 shows an exploded view of a discharger according to the present disclosure.
Figures 2A, 2B:
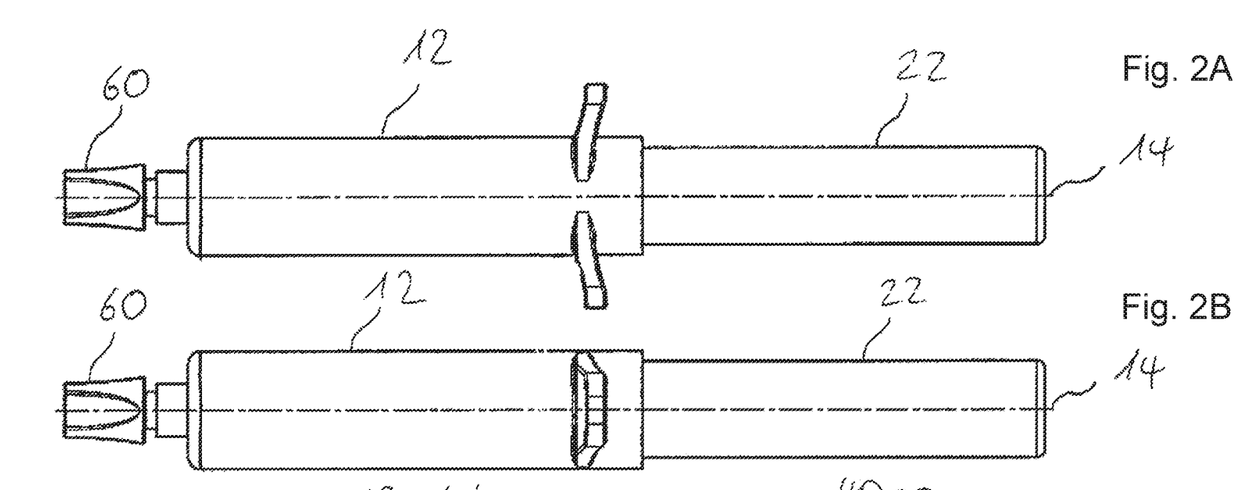
FIG. 2A and FIG. 2B show the discharger in an initial state with the container assuming its first position relative to the piston and the piston assuming its first position relative to the housing.
Figure 3A:
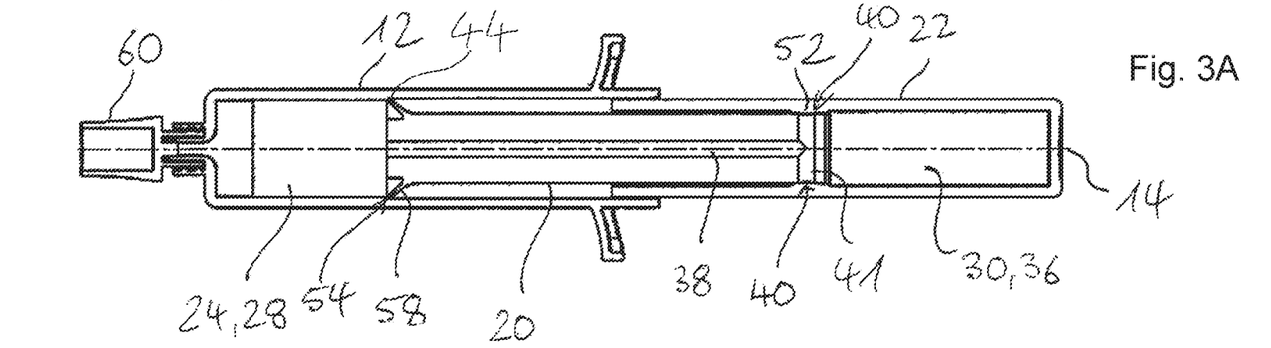
FIG. 3A and FIG. 3B show a sectional view of the discharger in the initial state.
Figures 3B, 5B:
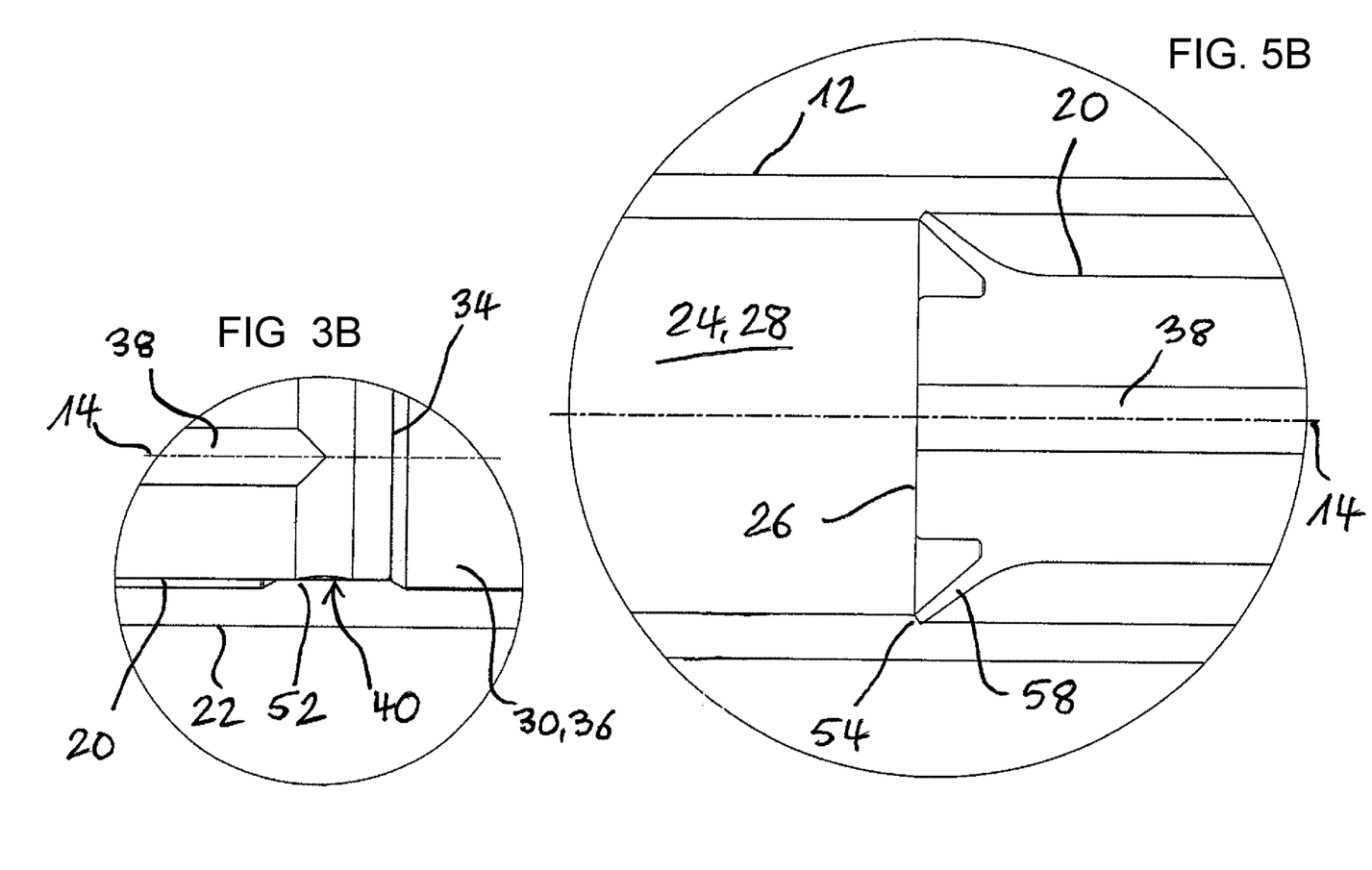
FIG. 5A and FIG. 5B show an enlarged detail of FIG. 4 including the releasable retaining means.
Figures 4, 5A, 6:
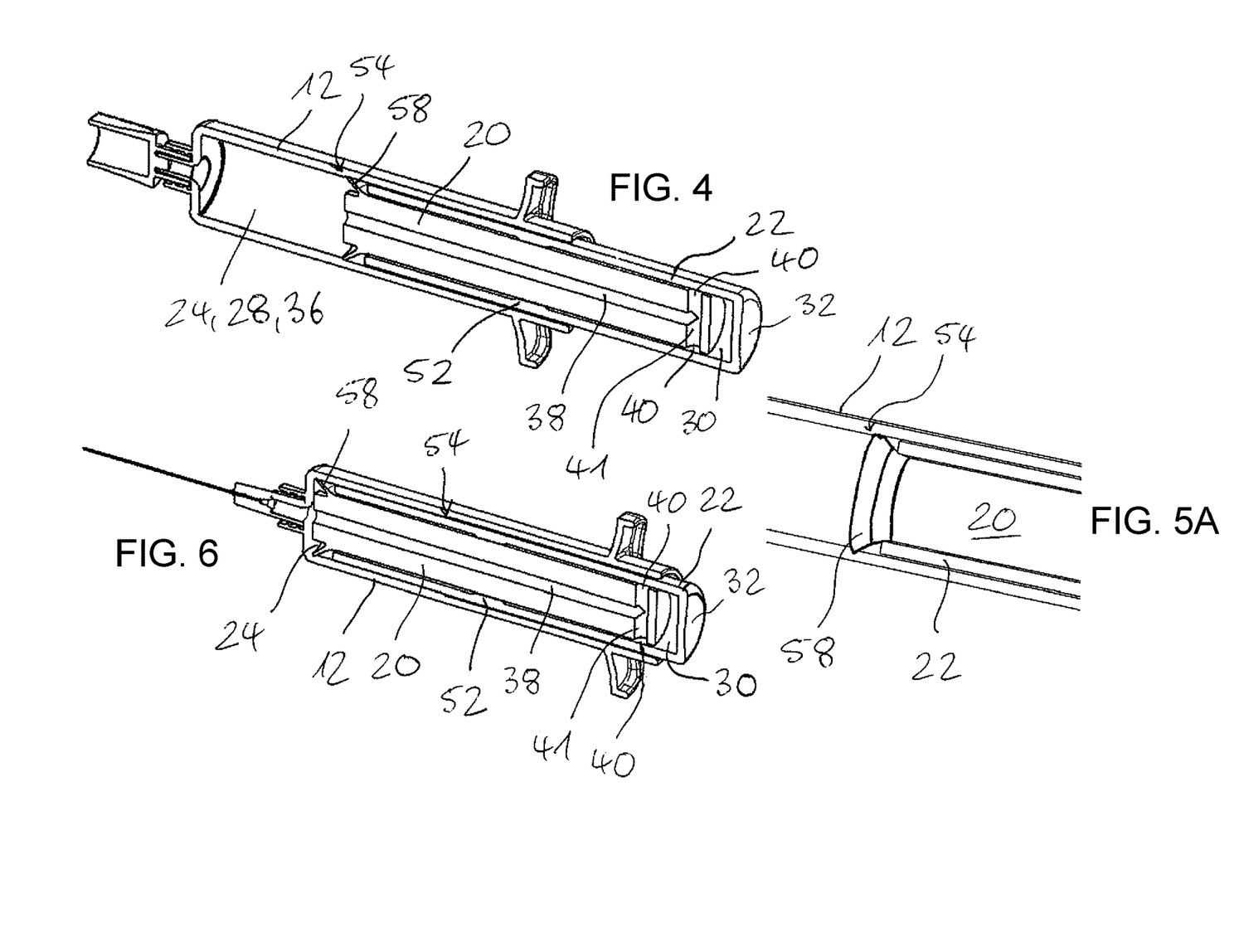
FIG. 4 shows a sectional view of the discharger in a state wherein the container is about to reach its second position.
FIG. 6 shows a sectional view of the discharger in the final state where the released piston has been pushed via the container into its second position.

The piston 20 is arranged at least partly inside the housing 12 and is axially moveable relative thereto between a first position (FIGS. 2A-2B, 3A-3B, 4, and 5A-5B) and a second position (FIG. 6).

The hollow cylindrical container 22 is also arranged at least partly inside the housing 12. The container 22 surrounds a proximal portion of the piston 20 and is axially moveable relative to the piston 20 between a first position (FIGS. 2A-2B and 3A-B) and a second position (FIGS. 4 and 6).

A first compartment 24 is defined within the housing 12 between the distal end 26 of the piston 20 assuming its first position and the distal end 18 of the housing 12 for storing at least one first component 28. A second compartment 30 is defined within the container 22 assuming its first position between the proximal end 32 of the container 22 and the proximal end 34 of the piston 20 for receiving a second component 36. At its proximal end 32, the container 22 is closed. The container 22 may be filled completely or partly with the second component 36 through its open distal end 56, i.e. the complete inner space of the container 22 or only a part thereof can form the second compartment 30 for the second component 36.

An axially extending passage 38 is disposed in the interior of the piston 20 and in communication with the first compartment 24 and peripheral openings 40 (FIGS. 3A-3B, 4 and 6) of the piston 20 in the region of the proximal end 34 of the piston 20. The peripheral openings 40 and the passage 38 are connected via a passage 41 extending radially with respect to the longitudinal axis 14.

A sealing means or element 52 is provided for preventing communication between the second compartment 30 and the peripheral openings 40 of the piston 20 when the container 22 assumes its first position.

A releasable retaining means or device 44 is provided for retaining the piston 20 in its first position until the container 22 has reached its second position.

Communication between the second compartment 30 and the peripheral openings 40 of the piston 20 is established after initiation of the movement of the container 22 out of its first position towards its second position relative to the piston 20. During that movement, the second component 36 is transmitted from the second compartment 30 into the first compartment 24 through the passage 38 of the piston 20, thereby bringing the first component and the second component together to form a substance to be discharged. The retaining device 44 is released by the container 22 reaching its second position.

With the further movement of the container 22 into the housing 12 and the simultaneous movement of the released piston 20 out of its first position towards its second position, the substance formed by the two components 28, 36 is pressed out of the first compartment 24 through the distal end 18 of the housing 12.

The container 22 assuming its first position protrudes beyond the proximal end 16 of the housing 12 so as to be pushable further onto the piston 20 out of its first position into its second position. The piston 20 assuming its first position protrudes beyond the proximal end 16 of the housing 12 so as to be pushable via the container 22 assuming its second position further into the housing 12 out of its first position into its second position.

The sealing element 52 is in the form of a circumferentially extending protrusion which projects inwardly from the inner wall of the container 22 towards the outer wall of the piston 20 so as to sealingly close the opening 40s of the piston 20 when the container 22 assumes its first position. The proximal end 34 of the piston 20 closes the open distal end 56 of the container 22 so as to prevent the second component 36 from getting out of the second compartment 30. When the container 22 starts moving towards its second position, the openings 40 of the piston 20 are opened by the sealing means 52 so that communication between the second compartment 30 and the first compartment 24 via the openings 40 and the passage 38 of the piston 20 is established.

The sealing element 52 also serve as positioning and guiding means or device for the piston 20 inside the container 22.

The container 22 may be adapted to be loaded with a cartridge defining the second compartment 30 for storing the second component 36. Alternatively, in the embodiment as shown in the figures, the container 22 is closed at its proximal end and not adapted to store either directly or indirectly by being loaded with e.g. a cartridge the second component 36 for a certain period of time. Rather, the container 22 has its open distal end 56 to be filled directly with the second component 36 when necessary. A closing device or means for closing the container 22 at its distal end so as to allow for the storage of the second component 36 over a short or long period of time may be provided but are not mandatory for the invention. Thus, the container 22 may be adapted to be filled with the second component 36 only immediately before the actual use of the discharger.

The releasable retaining device 44 comprises a peripheral stop 54 at the inner wall of the housing 12 on which a rim of the distal end 26 of the piston 20 assuming its first position abuts until it is pushed out of engagement with the stop 54 by the distal end 56 of the container 22 when the container 22 reaches its second position.

Specifically, the distal end 26 of the piston 20 includes a conically shaped portion 58 having an outer cross section increasing towards its distal end, the conically shaped portion 58 being flexibly deformable by the distal end 56 of the container 22 reaching its second position so as to push the rim of the conically shaped portion 58 out of engagement with the stop 54 and to release the retaining means 44.

The stop 54 is formed by a tapering of the inner cross section of the housing 12.

The discharger 10 may be adapted for being prefilled with at least one of the two components 28, 36. Specifically, as regards the container 22, the container 22 may be open at its distal end 56 to be closed only by the proximal end of the piston, for example after having been filled by a user with e.g. distilled water immediately before use of the discharger. Thus, instead of being prefilled with a fluid or adapted to be loaded with a cartridge, which is prefilled with a fluid, the container is only filled with the desired fluid immediately before use, e.g. before actually applying a vaccine to a patient. Thus, storing a fluid as the second component over a period of time is possible with but not mandatory for the invention, In the first compartment 24, the two components 28, 36 can be mixed, or one component 28 can be wetted by another component 36.

Any components can be mixed and/or combined and/or brought together to make up the substance to be discharged. The discharger 10 may be used for discharging a substance including at least one medical, dental or veterinary agent, for example a vaccine, and/or for discharging a substance of any other kind comprising at least two components.

The invention claimed is:

1. A discharger for discharging a predetermined amount of a substance including at least two components, the discharger comprising:
   a housing defining a longitudinal axis and having a proximal end and a distal end;
   a piston arranged at least partly inside the housing and being axially movable relative thereto between a first piston position and a second piston position;
   a hollow cylindrical container arranged at least partly inside the housing, the container surrounding the piston at least partly and being axially movable relative to the piston between a first container position and a second container position;
   wherein when the container is in the first container position, the container protrudes beyond the proximal end of the housing so as to be pushable further onto the piston out of first container position into the second container position;
   at least one first compartment defined within the housing between the distal end of the piston when the piston is in the first piston position and the distal end of the housing for receiving at least one first component of the components,
   at least one second compartment defined within the container when the container is in the first container position between a closed proximal end of the container and the proximal end of the piston for receiving at least one second component of the components,
   an axially extending passage in the interior of the piston and in communication with the first compartment and at least one peripheral opening of the piston in the region of the proximal end of the piston;
   a sealing element configured to prevent communication between the second compartment and the peripheral opening of the piston when the container is in the first container position; and
   a releasable retaining device configured to retain the piston in the piston first position until the container has reached the second container position,
   the discharger further being configured so that
   communication between the second compartment and the peripheral opening of the piston is established after initiation of the movement of the container out of the container first position towards the container second position relative to the piston, thereby transferring the second component from the second compartment into the peripheral opening and through the passage of the piston into the first compartment,
   the retaining device being released by the container reaching the second container position, and
   with the further movement of the container into the housing and the simultaneous movement of the piston out of the piston first position towards the piston second position, the at least two components are pressed out of the first compartment through the distal end of the housing.

2. The discharger according to claim 1, wherein the sealing element comprises a circumferentially extending projection which projects inwardly from an inner wall of the container towards an outer wall of the piston so as to sealingly close the peripheral opening of the piston when the container is in the first container position, and to contact the piston in a region located distal to the peripheral opening when the container is in a position with the communication between the second compartment and the peripheral opening being established after initiation of the movement of the container out of the first container position towards the second container position relative to the piston.

3. The discharger according to claim 1,
   wherein the container is configured to be loaded with a cartridge defining the second compartment for storing the second component, or the container is a cartridge which is loaded into or which is configured to be loaded into the housing and which defines the second compartment for storing the second component.

4. The discharger according to claim 1,
   wherein the piston has an axial length along the longitudinal axis which is approximately the same as an axial length of the housing or of the container, or is between 0.5 and 1.5 times the axial length of the housing or of the container.

5. The discharger according to claim 1,
   wherein the piston has an axial length along the longitudinal axis which is larger than a diameter thereof as measured perpendicular to the longitudinal axis, or which is more than 2 times the diameter thereof as measured perpendicular to the longitudinal axis.

6. The discharger according to claim 1,
   wherein the releasable retaining device comprises a stop at an inner wall of the housing on which a rim of the distal end of the piston in the first piston positions abuts until the piston is pushed out of engagement with the stop by the distal end of the container when the container reaches the second container position.

7. The discharger according to claim 6,
   wherein the distal end of the piston includes a conically shaped portion having an outer cross section increasing towards a distal end thereof, and the conically shaped portion of the piston is flexibly deformable by the distal end of the container reaching the second container position so as to push the rim of the distal end of the piston out of engagement with the stop and to release the retaining device.

8. The discharger according to claim 6,
wherein the stop is formed by a tapering of an inner cross section of the housing.

9. The discharger according to claim 1,
wherein the discharger is prefilled with or is capable of being prefilled with at least one of the at least two components.

10. The discharger according to claim 1,
wherein the first component of the at least two components is a desiccant, and the second component of the at least two components is a fluid.

11. The discharger according to claim 1, further comprising a cartridge including the second component which is configured, together with the first component within the discharger, to form a substance to be discharged by the discharger.

12. A discharge system comprising:
a discharger according to claim 11, the cartridge configured to be loaded into the container of the discharger, or the cartridge is the container of the discharger.

13. A method of operating a discharger according to claim 1, the method comprising:
discharging a substance including at least one medical, dental or veterinary agent via the discharger.

14. The discharger according to claim 1,
wherein the piston has an axial length along the longitudinal axis which is between 0.8 and 1.2 times an axial length of the housing or of the container.

15. The discharger according to claim 1,
wherein the piston has an axial length along the longitudinal axis which is between 4 and 6 times a diameter thereof as measured perpendicular to the longitudinal axis.

16. The discharger according to claim 1,
wherein the discharger is an expendable syringe.

17. The discharger according to claim 1,
wherein when the piston is in the first piston position, the piston protrudes beyond the proximal end of the housing so as to be pushable via the container further into the housing out of the first piston position into the second piston position.

18. The discharger according to claim 1, wherein the releasable retaining device is configured to engage with the housing in a retaining condition and the retaining device is released when the container reaches the second container position and disengages the retaining device from the housing.

19. The discharger according to claim 1, wherein after the initiation of the movement of the container and after establishment of the communication between the second compartment and the peripheral opening of the piston, further movement of the container towards the second container position effects the transferring of the second component form the second compartment into the peripheral opening and through the passage of the piston into the first compartment.

* * * * *